United States Patent
Masuo et al.

(10) Patent No.: US 8,155,266 B2
(45) Date of Patent: Apr. 10, 2012

(54) FLUOROSCOPY

(75) Inventors: Katsuhiro Masuo, Kyoto (JP);
Masahiro Tanaka, Kyoto (JP);
Mikihiko Kato, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 198 days.

(21) Appl. No.: 12/672,420

(22) PCT Filed: Jun. 12, 2008

(86) PCT No.: PCT/JP2008/060781
§ 371 (c)(1),
(2), (4) Date: Feb. 5, 2010

(87) PCT Pub. No.: WO2009/019935
PCT Pub. Date: Feb. 12, 2009

(65) Prior Publication Data
US 2011/0096899 A1 Apr. 28, 2011

(30) Foreign Application Priority Data
Aug. 7, 2007 (JP) .................................. 2007-205228

(51) Int. Cl.
*A61B 6/02* (2006.01)

(52) U.S. Cl. .......................................... 378/42; 378/62

(58) Field of Classification Search .................... 378/62, 378/195, 196, 197
See application file for complete search history.

(56) References Cited

U.S. PATENT DOCUMENTS

| 6,208,710 | B1 * | 3/2001 | Nagai ........................... 378/108 |
| 6,549,609 | B1 | 4/2003 | Iinuma et al. |
| 2002/0051517 | A1 * | 5/2002 | Schwieker .................... 378/196 |
| 2002/0141539 | A1 | 10/2002 | Iinuma |
| 2004/0131154 | A1 | 7/2004 | Watanabe et al. |

FOREIGN PATENT DOCUMENTS

| CN | 1293532 | 5/2001 |
| JP | 2001-238875 | 9/2001 |
| JP | 2002-028155 | 1/2002 |
| JP | 2002-078707 | 3/2002 |
| JP | 2003-010164 | 1/2003 |
| JP | 2005-031323 | 2/2005 |

OTHER PUBLICATIONS

Chinese First Examination Report of China Application No. 200880102198.7, dated Jan. 31, 2011.

* cited by examiner

*Primary Examiner* — Hoon Song
(74) *Attorney, Agent, or Firm* — J.C. Patents

(57) ABSTRACT

When urinary organ contrasting inspection is performed by using a fluoroscopy for digestive organs, a region of interest such as a bladder often comes to a vicinity of a foot side end of a table top. Consequently, it is often the case that an irradiation field cannot be limited to a suitable area with respect to the region of interest and only an oblique photography can be performed. When the urinary organ contrasting inspection is performed, an X-ray tube device (1), an X-ray diaphragm (16), and an X-ray image detector (3) are interlocked to enable a foot side end of the irradiation field to be consistent with a foot side end of the X-ray image detector (3). Thus, a focal point (1A) of the X-ray tube device (1) can be moved directly above the foot side end of the X-ray image detector (3).

6 Claims, 8 Drawing Sheets

FLUOROSCOPY

BACKGROUND OF THE INVENTION

1. Field of the Invention

The present invention relates to a fluoroscopy.

2. Description of Related Art

As shown in FIG. 2, a fluoroscopy for digestive organs includes, for example, a table top 4, an X-ray tube device 1, an X-ray diaphragm 16, and an X-ray image detector 3 etc. The table top 4 is held by using a main column 5 vertically standing on a floor through a base 6, so as to carry a subject (not shown). The X-ray tube device 1 is held by using an arm 26 mounted on a column 2, and the column 2 is movably held in a length direction of the table top 4 by using the main column 5. The X-ray diaphragm 16 is mounted on an X-ray irradiating section of the X-ray tube device 1 and opens or closes a rectangular irradiation field. The X-ray image detector 3 is arranged on a back side of the table top 4 opposite to the X-ray tube device 1, and is movably held in the length direction of the table top 4 by using the table top 4, and includes, for example, a flat-panel-type X-ray detector or a cassette having a built-in film. Furthermore, the X-ray tube device 1 and the X-ray image detector 3 are generally configured in the following manner, that is, the X-ray tube device 1 and the X-ray image detector 3 are moved parallel to the table top 4 while maintaining a fixed position relation between each other through a mechanical combination of the parts for holding the X-ray tube device 1 and the X-ray image detector 3, or through a control motion of a control section (not shown) formed by, for example, a microcomputer as disclosed in, for example, Japanese Patent Laid-open Publication No. 2002-28155 (hereafter referred to as "Patent Document 1").

Particularly, in the fluoroscopy for digestive organs, considering the position relation between the X-ray tube device 1 and the X-ray image detector 3, a focal point (not shown in FIG. 2) of the X-ray tube device 1 is always arranged directly above a central position of the X-ray image detector 3. Therefore, as shown in FIG. 12, when one end of the X-ray image detector 3 comes to one end of the table top 4, a focal point 1A is located directly above a detector center 3A of the X-ray image detector 3, so as to become a moving limit position of one side of the X-ray tube device 1. Here, the position is temporarily called a first moving limit position. Furthermore, in the digestive organ contrasting photography, a region of interest for the photography is not located in the vicinity of the end of the table top 4, such that a practical moving limit position of the X-ray tube device 1 is set at a suitable position of one side that is nearer to the center of the length direction of the table top 4 as compared with the first moving limit position. In addition, in FIGS. 12, 21 and 22 represent two irradiation fields having different sizes, and the irradiation fields are described in the following. In addition, the reference numerals in FIG. 12 the same as that in FIG. 2 indicate the same parts as that in FIG. 2, so that the descriptions thereof are omitted.

The fluoroscopy for digestive organs is configured in the above manner, but recently the fluoroscopy for digestive organs with the above configuration is used in a urinary organ contrasting inspection. FIG. 10 shows a situation of urinary organ contrasting photography using the fluoroscopy for digestive organs. However, a catheter is inserted into the urethra of a subject 7 from a foot side of the subject 7, such that a foot rest 17 for placing feet of the subject 7 is mounted on a foot side end of the table top 4, and thus the subject 7 is carried on the table top 4 in a manner of being close to the foot side of the table top 4. Next, when the table top 4 is rotated or the subject 7 is moved after the catheter is inserted, the body of the subject 7 bears a heavy burden, such that it is necessary to perform the photography on the original position as much as possible. As a result, in the urinary organ contrasting photography, the region of interest, for example, a bladder 7A, is often located in the vicinity of the end of the table top 4.

Therefore, in order to enable the fluoroscopy for digestive organs to be used in the urinary organ contrasting inspection, most devices expand the setting of the practical moving limit position of the X-ray tube device 1 to the first moving limit position. As a result, even if the subject 7 is carried on the table top 4 in a manner of being close to the foot side of the table top 4 as shown in FIG. 10, and the bladder 7A serving as the region of interest is located in the vicinity of the end of the table top 4, by moving the X-ray tube device 1 to the first moving limit position, and operating the X-ray diaphragm 16 to set the irradiation field to become as wide as, for example, the irradiation field 21, the photography is performed on the bladder 7A. Furthermore, when the bladder 7A is located on one side slightly closer to the center of the table top 4, the setting of the irradiation field is altered in such a way that the irradiation field 21 as shown in FIG. 12 is replaced by the slightly narrower irradiation field 22 for covering the bladder 7A, thereby alleviating the over-irradiation on the subject 7. In addition, the reference numerals in FIG. 10 the same as that in FIG. 12 indicate the same parts as that in FIG. 12, so that the descriptions thereof are omitted.

PROBLEMS TO BE SOLVED IN THE INVENTION

The method for performing urinary organ contrasting inspection by using the fluoroscopy for digestive organs has been described above. However, under such a situation, according to the reasons, as shown in FIG. 10, the bladder 7A serving as the region of interest often comes to a vicinity of the end of the table top 4. Therefore, an operator (not shown) firstly arranges the X-ray tube device 1 on the first moving limit position, and arranges one end of the X-ray image detector 3 at a position of coming to the end of the table top 4 due to an interlocking relation. Then, the X-ray diaphragm 16 is operated in such a way that the irradiation field is set to be as wide as, for example, the irradiation field 21, and then the photography is performed. In this manner, although the photography is performed on the bladder 7A, the bladder 7A is located in the vicinity of the end in the irradiation field 21, such that in order to cover the bladder 7A, the photography must be performed with the irradiation field having a size being much larger than the required minimum size, and as a result, the subject 7 is over-irradiated.

In addition, the photography is performed when the region of interest is arranged in the end of the irradiation field 21 instead of in a center position of the irradiation field 21. Thus, a so-called oblique photography is performed on the region of interest, in which the X rays are obliquely incident into the X-ray image detector 3, and thus as compared with the situation that the region of interest is arranged at the center position of the irradiation field 21 and the photography is performed by using the X-ray beams close to the X-ray center, the picture blurring and picture distortion problems become serious.

Before performing the photography, the operator performs positioning to locate the region of interest above the X-ray image detector 3. However, when the region of interest is located in vicinity of the end of the X-ray image detector 3, even if the region of interest is located above the X-ray image detector 3, X rays obliquely pass through the region of interest, such that the picture is exposed out of the X-ray image detector 3. Here, the positioning and the photography must be performed once again, thereby increasing the burden of the subject 7 and the operator.

In order to eliminate the over-irradiation, the following situation exists. A single acting diaphragm 19 as shown in FIG. 11 is used to replace the X-ray diaphragm 16 capable of enabling the size of the irradiation field to be expanded or narrowed down symmetrically on the left and right side with respect to a center axis of the irradiation field. The single acting diaphragm 19 is capable of enabling the size of the irradiation field to be expanded or narrowed down asymmetrically on the left and right side with respect to the center axis of the irradiation field, thereby obtaining an irradiation field 18 of, for example, covering only a half of the foot side from the center axis of the irradiation field to replace the irradiation field 21 of FIG. 10. Although the over-irradiation on the subject 7 is greatly eliminated by using the single acting diaphragm 19, the picture blurring and picture distortion problems resulting from the oblique photography cannot be solved.

SUMMARY OF THE INVENTION

Accordingly, the present invention is directed to a fluoroscopy, which is capable of solving a problem that a subject 7 is over-irradiated when urinary organ contrasting inspection is performed by using a fluoroscopy for digestive organs, solving the picture blurring and picture distortion problems resulting from an oblique photography, and alleviating burdens of the subject 7 and an operator during the inspection. In addition, the reference numerals in FIG. 11 the same as that in FIG. 12 indicate the same parts as that in FIG. 12, so that the descriptions thereof are omitted.

According to one aspect of the present invention, it is to provide a fluoroscopy, comprising: a table top, for carrying a subject; an X-ray tube, movably held in a body axis direction of the subject parallel to the table top; an X-ray image detector, arranged opposite to the X-ray tube by sandwiching the table top there-between, and being movable in the body axis direction of the subject parallel to the table top; and an X-ray diaphragm, mounted on the X-ray tube and forming an X-ray irradiation field The fluoroscopy further comprises a control means therein, and when the X-ray irradiation field is narrower than a detecting area of the X-ray image detector, the control means controls the X-ray tube or the X-ray image detector to be moveable such that a foot side end of the X-ray irradiation field unexceeds a foot side end of the X-ray image detector.

According to another aspect of the present invention, it is to provide a fluoroscopy, comprises: a table top, for carrying a subject; an X-ray tube, movably held in a body axis direction of the subject parallel to the table top; an X-ray image detector, arranged opposite to the X-ray tube by sandwiching the table top there-between, and being movable in the body axis direction of the subject parallel to the table top; and an X-ray diaphragm, mounted on the X-ray tube and forming a rectangular X-ray irradiation field. The fluoroscopy further comprises a control means and a control manner assigning means. The control means performs a control in one of a first control manner and a second control manner. In the first control manner, the X-ray tube and the X-ray image detector are moved parallel to the table top in such a way that a focal point of the X-ray tube is located directly above a center of the X-ray image detector. In the second control manner, when the X-ray irradiation field is altered on ends of the X-ray tube and the X-ray image detector being moved to a foot side of the subject parallel to the table top, the X-ray tube is moved in such a way that a foot side end of the X-ray irradiation field and a foot side end of the X-ray image detector are overlapped. The control manner assigning means assigns the control means to perform the control in the first control manner or in the second control manner.

In the fluoroscopy, a camera part assigning means for assigning a camera part in the first control manner or in the second control manner according to the camera part also serves as the control manner assigning means.

In the fluoroscopy, the control manner assigning means is a change-over switch.

According to further another aspect of the present invention, it is to provide a fluoroscopy, comprising: a table top, for carrying a subject; an X-ray tube, movably and rotatably held in a body axis direction of the subject parallel to the table top; an X-ray image detector, arranged opposite to the X-ray tube by sandwiching the table top there-between, and being movable in the body axis direction of the subject parallel to the table top; and an X-ray diaphragm, mounted on the X-ray tube and forming a rectangular X-ray irradiation field. The fluoroscopy further comprises a control means and a control manner assigning means. The control means performs a control in one of a first control manner and a second control manner. In the first control manner, the X-ray tube and the X-ray image detector are moved parallel to the table top in such a way that a focal point of the X-ray tube is located directly above a center of the X-ray image detector. In the second control manner, when the X-ray irradiation field is altered on ends of the X-ray tube and the X-ray image detector being moved to a foot side of the subject parallel to the table top, the X-ray tube is rotated in such a way that a foot side end of the X-ray irradiation field and a foot side end of the X-ray image detector are overlapped. The control manner assigning means assigns the control means to perform the control in the first control manner or in the second control manner.

In the fluoroscopy, a camera part assigning means for assigning a camera part in the first control manner or in the second control manner according to the camera part also serves as the control manner assigning means.

In the fluoroscopy, the control manner assigning means is a change-over switch.

EFFECT OF THE INVENTION

When the urinary organ contrasting inspection is performed through the fluoroscopy of the present invention, the X-ray tube device, the X-ray diaphragm, and the X-ray image detector are always interlocked in such a way that the foot side end of the rectangular irradiation field is consistent with the foot side end of the X-ray image detector. Therefore, even if the region of interest for the photography is located in vicinity of the foot side end of the X-ray image detector, the subject can be prevented from being over-irradiated through the common X-ray diaphragm, and the picture blurring and picture distortion problems resulting from the oblique photography are solved. In addition, since an approximate center of the X-ray beam passes through the region of interest, the situation that a picture of the region of interest arranged on the X-ray image detector is exposed out of the X-ray image detector is greatly decreased, thereby alleviating the burden of the subject and the operator resulting from the re-positioning operation.

BRIEF DESCRIPTION OF THE DRAWINGS

The accompanying drawings are included to provide a further understanding of the invention, and are incorporated

DESCRIPTION OF THE EMBODIMENTS

Figure 1:
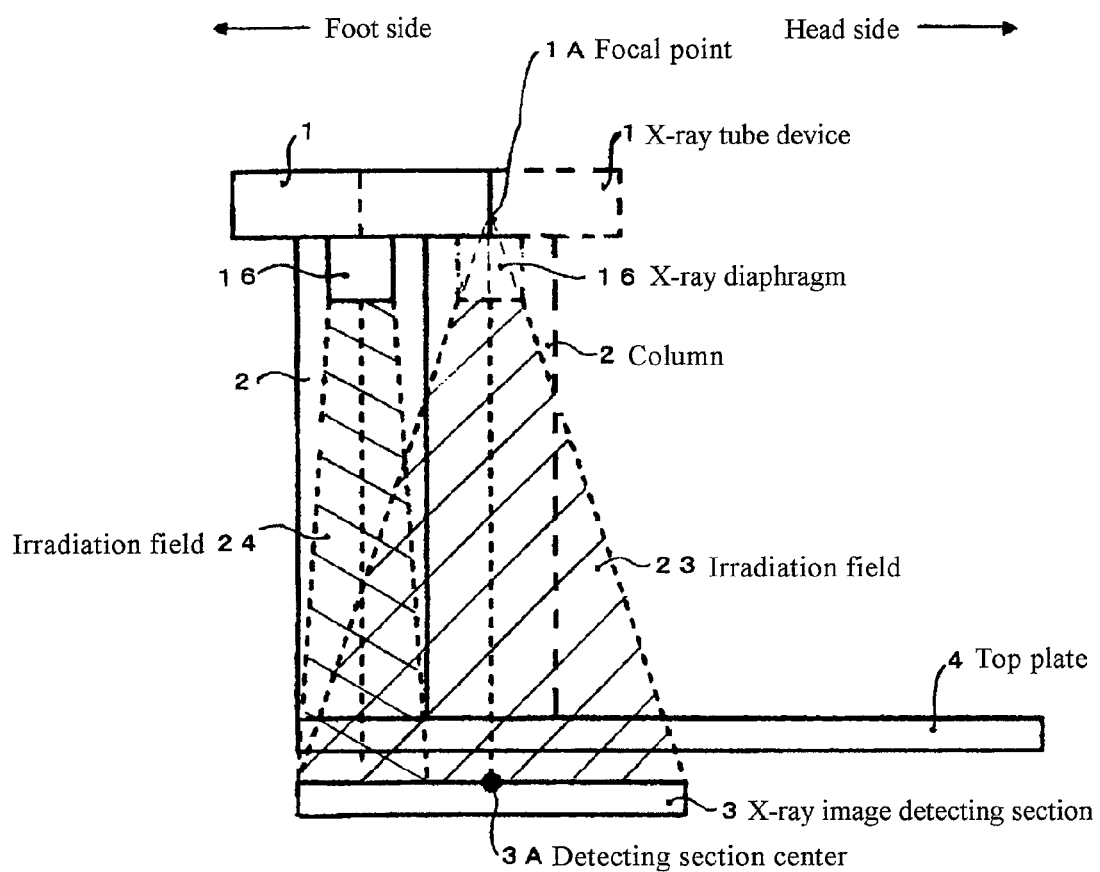
FIG. 1 is a view for expressing motions of a fluoroscopy according to a first embodiment of the present invention.

Reference will now be made in detail to the present embodiments of the invention, examples of which are illustrated in the accompanying drawings. Wherever possible, the same reference numbers are used in the drawings and the description to refer to the same or like parts.

Considering the moving motions of an X-ray tube device and an X-ray image detector, it is switched between interlocking the X-ray tube device and the X-ray image detector to enable a focal point of the X-ray tube device to come to directly above a central position of the X-ray image detector and interlocking the X-ray tube device and the X-ray image detector to enable a foot side end of an irradiation field to be consistent with a foot side end of the X-ray image detector, according to whether "digestive organ inspection" or "urinary organ inspection" is selected on an inspection menu screen.

First Embodiment

Figure 2:
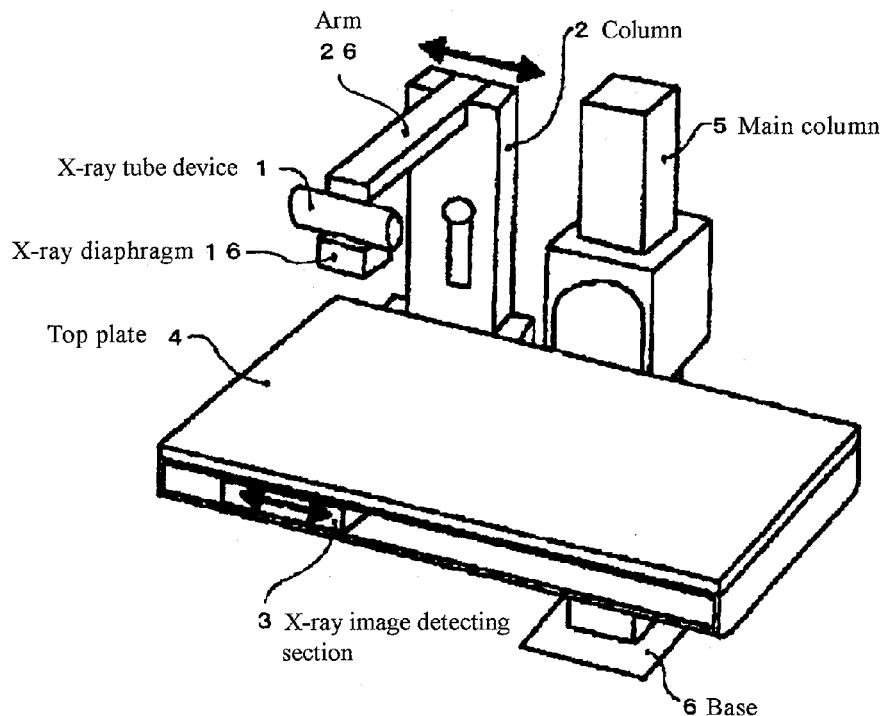
FIG. 2 is a structural view of a fluoroscopy.
Figure 3:
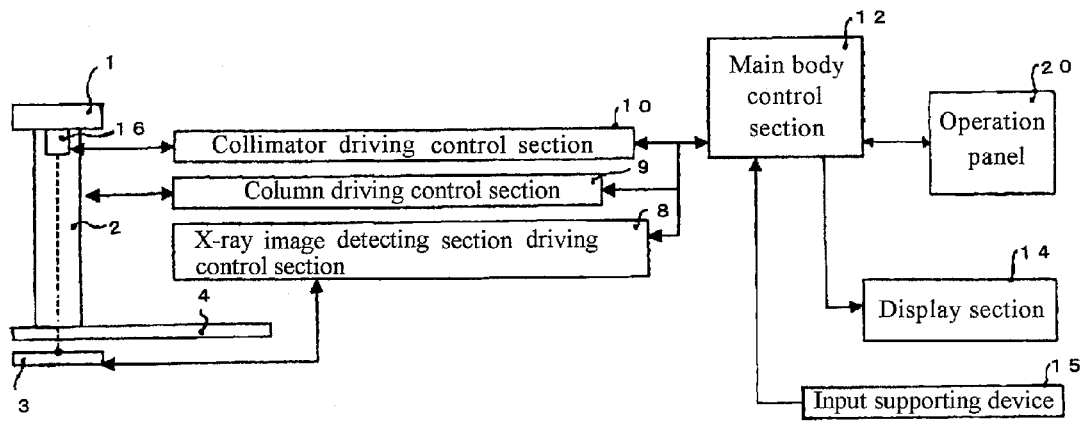
FIG. 3 is a block diagram for expressing motions of the fluoroscopy according to the first embodiment of the present invention.
Figure 4:
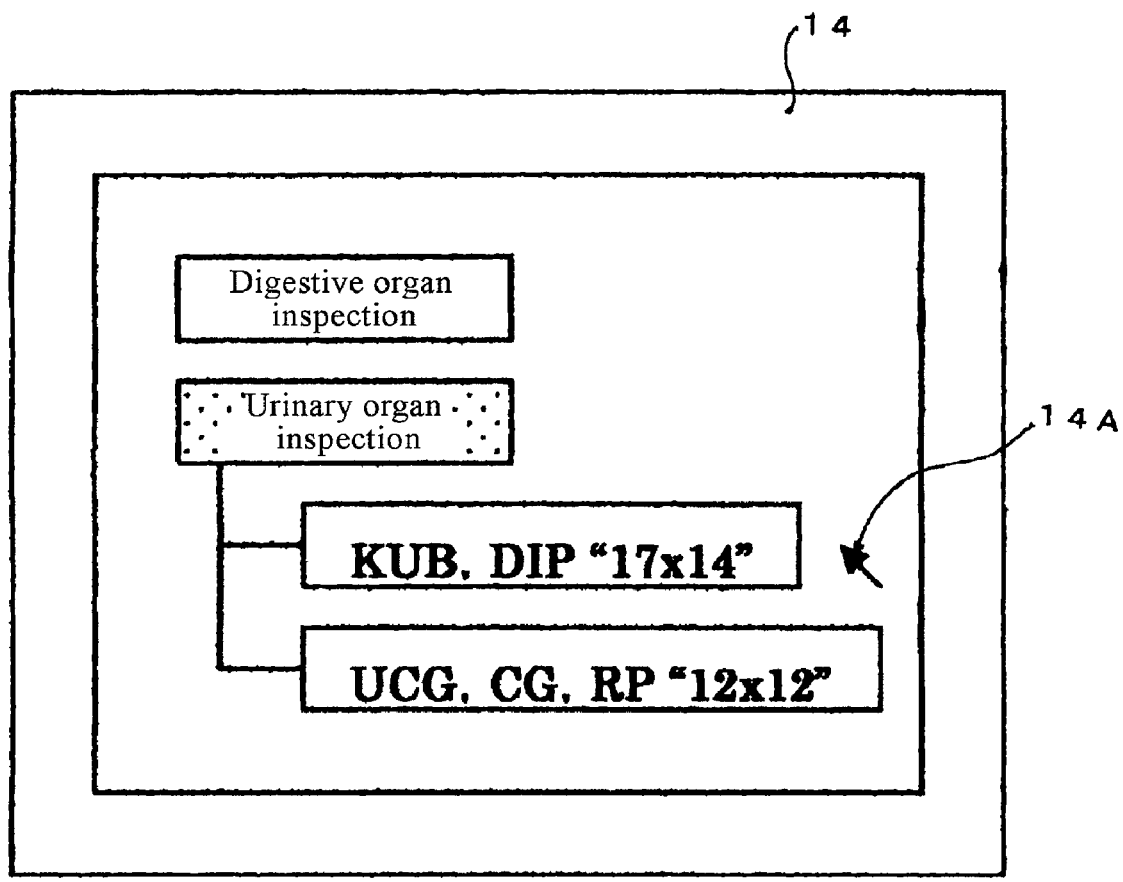
FIG. 4 is a view of a displaying example of a display section of the fluoroscopy according to the first embodiment of the present invention.

Referring to FIGS. 1 to 5, the first embodiment of the present invention is described. FIG. 2 is a view of an external appearance of a fluoroscopy according to the first embodiment of the present invention. FIG. 3 is a block diagram for demonstrating a control section for controlling the characteristic motions of the first embodiment of the present invention and an operation section. In addition, FIG. 4 is a view of a displaying example of a display section 14, and FIG. 1 is a view for demonstrating a position relation between an X-ray tube device 1 and an X-ray image detector 3 being interlocked with each other.

As shown in FIG. 2, the fluoroscopy according to the first embodiment of the present invention includes, for example, a table top 4, an X-ray tube device 1, an X-ray diaphragm 16, and an X-ray image detector 3. The table top 4 is held by using a main column 5 vertically standing on a floor through a base 6, so as to carry a subject (not shown). The X-ray tube device 1 is held by using an arm 26 mounted on a column 2, and the column 2 is movably held in a length direction of the table top 4 by using the main column 5. The X-ray diaphragm 16 is mounted on an X-ray irradiating section of the X-ray tube device 1 and opens or closes a rectangular irradiation field. The X-ray image detector 3 is arranged on a back side of the table top 4 opposite to the X-ray tube device 1, and is movably held in the length direction of the table top 4 by using the table top 4, and includes, for example, a flat-panel-type X-ray detector or a cassette having a built-in film.

Furthermore, the operator (not shown in FIG. 3) selects the "digestive organ inspection" from the inspection menu, for example, shown in FIG. 4 and displayed in the display section 14 as shown in FIG. 3 by operating an input supporting device 15 formed by, for example, a mouse to move a cursor 14A. Then, the operator operates the operation panel 20, such that the column 2 for holding the X-ray image detector 3 and the X-ray tube device 1 is moved parallel to the table top 4. At this time, a main body control section 12 formed by, for example, a microcomputer, controls an X-ray image detector driving control section 8 and a column driving control section 9, so as to perform an interlocking control to enable a focal point (not shown in FIG. 2) of the X-ray tube device 1 to be always arranged directly above a central position of the X-ray image detector 3. In addition, the reference numerals in FIG. 3 the same as that in FIG. 2 indicate the same parts as that in FIG. 2, so that the descriptions thereof are omitted.

Therefore, as shown in FIG. 1, when one end of the X-ray image detector 3 comes to one end of the table top 4, a focal point 1A is located on a position of the X-ray tube device 1 directly above the central position of the X-ray image detector 3, that is, the position of the X-ray tube device 1 marked by dashed lines becomes a moving limiting position on one side of the X-ray tube device 1. The position is a first moving limit position. However, in digestive organ contrasting inspection, as described above, a region of interest for the photography is not located in vicinity of the end of the table top 4, so as to fully assure a moving area required by the X-ray tube device 1.

In another aspect, when urinary organ contrasting inspection is performed by using the fluoroscopy according to the first embodiment of the present invention, after the operator selects the "urinary organ inspection" from the display screen as shown in FIG. 4 in the same manner, the main body control section 12 of FIG. 3 controls the X-ray diaphragm 16 through a collimator driving control section 10, so as to adjust a size of the irradiation field to enable two ends of the irradiation field to be respectively consistent with two ends of the X-ray image detector 3. When the "urinary organ inspection" is selected, the main body control section 12 controls the X-ray tube device 1, the X-ray image detector 3, and the X-ray diaphragm 16 to be always interlocked to enable a foot side end of the irradiation field to be consistent with a foot side end of the X-ray image detector 3.

Under this state, in order to perform the photography on the subject (not shown in FIG. 3) carried in vicinity of a foot side of the table top 4, the operator operates the operation panel 20, such that the X-ray image detector 3 is moved to the foot side in parallel to the table top 4, until the foot side end of the X-ray image detector 3 as shown in FIG. 1 comes to the foot side end of the table top 4. At this time, the X-ray tube device 1 is interlocked to enable the foot side end of the irradiation field to be consistent with the foot side end of the X-ray image detector 3, such that the X-ray tube device 1 is moved till it reaches the position that the focal point 1A is located directly above the central position of the X-ray image detector 3, that is, the position of the X-ray tube device 1 marked by the dashed lines (that is, the first moving limit position).

Then, the operator operates the operation panel 20 to reduce the size of the irradiation field. After an irradiation field 23 is altered to, for example, an irradiation field 24, the main body control section 12 does not move the X-ray image detector 3, but moves the X-ray tube device 1 to enable the foot side end of the irradiation field to be consistent with the foot side end of the X-ray image detector 3, such that the X-ray tube device 1 is moved from the position that the focal point 1A is located directly above the central position of the X-ray image detector 3 and marked by the dashed lines of FIG. 1 towards the position in vicinity of the foot side marked by real lines.

Figure 5:
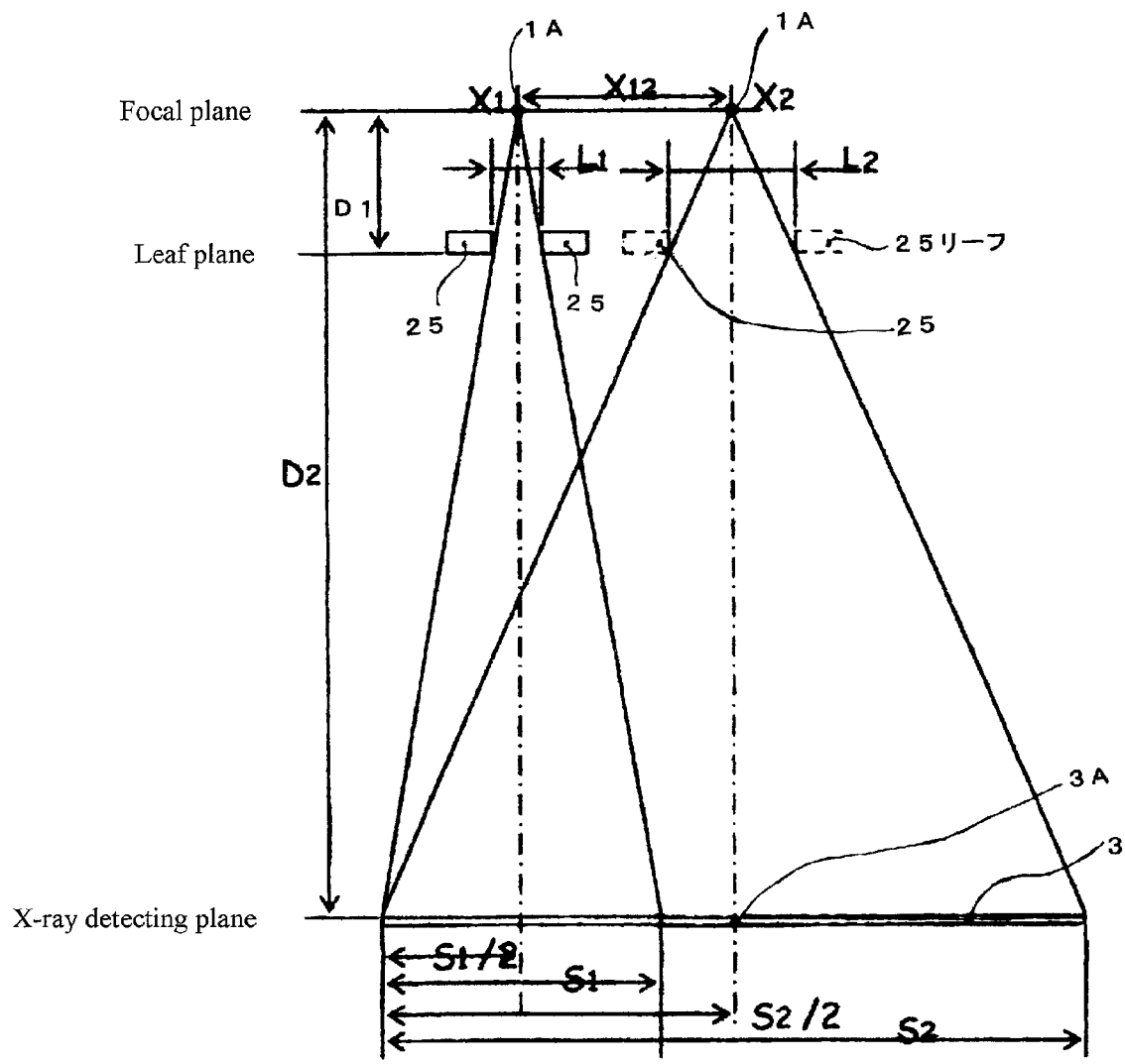
FIG. 5 is a view of a relation between an opening change of an X-ray diaphragm and a moving distance of a column according to the first embodiment of the present invention.

FIG. 5 shows a geometrical system diagram for calculating a moving distance X12 of the X-ray tube device 1 when an aperture width between two leaves 25 is altered from L2 to L1. The two leaves 25 are built in the X-ray diaphragm 16 (shown in FIG. 2), and are formed by X-ray shields for determining the irradiation field. The reference numerals in FIG. 5 the same as that in FIG. 1 indicate the same parts as that in FIG. 1, so that the descriptions thereof are omitted. It is assumed that a distance between a focal plane and a leaf plane is made to be D1, a distance between the focal plane and an X-ray detecting plane is made to be D2, and a length of the X-ray image detector 3 is made to be S2, and when the aperture width between the leaves 25 is narrowed from L2 to L1, the moving distance X12 of the X-ray tube device 1 is calculated by the main body control section 12 as shown in FIG. 3 according to the following Equation (1). Thus, the main body control section 12 controls the column driving control section 9 in such a way that the X-ray image detector 3 is not moved but the X-ray tube device 1 is moved for X12 towards the foot side.

$$X12 = S2/2 - S1/2 = D2*(L2-L1)/(2*D1) \quad \text{Equation (1)}$$

In addition, in FIG. 5, X1 and X2 are positions of the focal point 1A when the aperture width between the leaves 25 is L1 and L2 respectively, and S1 is the size of the irradiation field on the X-ray detecting plane when the aperture width between the leaves 25 is L1. In addition, the values of D1 and D2 are pre-stored in the main body control section 12 as shown in FIG. 3, and L1 and L2 are numerical values output from the main body control section 12 to the collimator driving control section 10 according to an instruction from the operation panel 20, such that the main body control section 12 performs the calculation of Equation (1) by using the numerical values.

The corresponding result is as shown in FIG. 1, and even after the foot side end of the X-ray image detector 3 comes to the foot side end of the table top 4, if the irradiation field is narrowed down by the X-ray diaphragm 16, merely the X-ray tube device 1 is further moved towards the foot side of the table top 4, and is moved till it reaches the position that the focal point 1A is located directly above the foot side end of the X-ray image detector 3 when the irradiation field is completely closed. Therefore, even in the urinary organ contrasting inspection when the region of interest for the photography is located in vicinity of the foot side end of the table top 4, the subject (not shown in FIG. 1) is prevented from being over-irradiated through the common X-ray diaphragm 16, and the picture blurring and picture distortion problems resulting from an oblique photography are solved. In addition, the X rays approximately vertically pass through the region of interest, such that the situation that a picture of the region of interest arranged on the X-ray image detector 3 is exposed out of the X-ray image detector 3 is reduced, thereby alleviating the burden of the subject and the operator (not shown in FIG. 1) resulting from the re-positioning operation.

Figure 12:
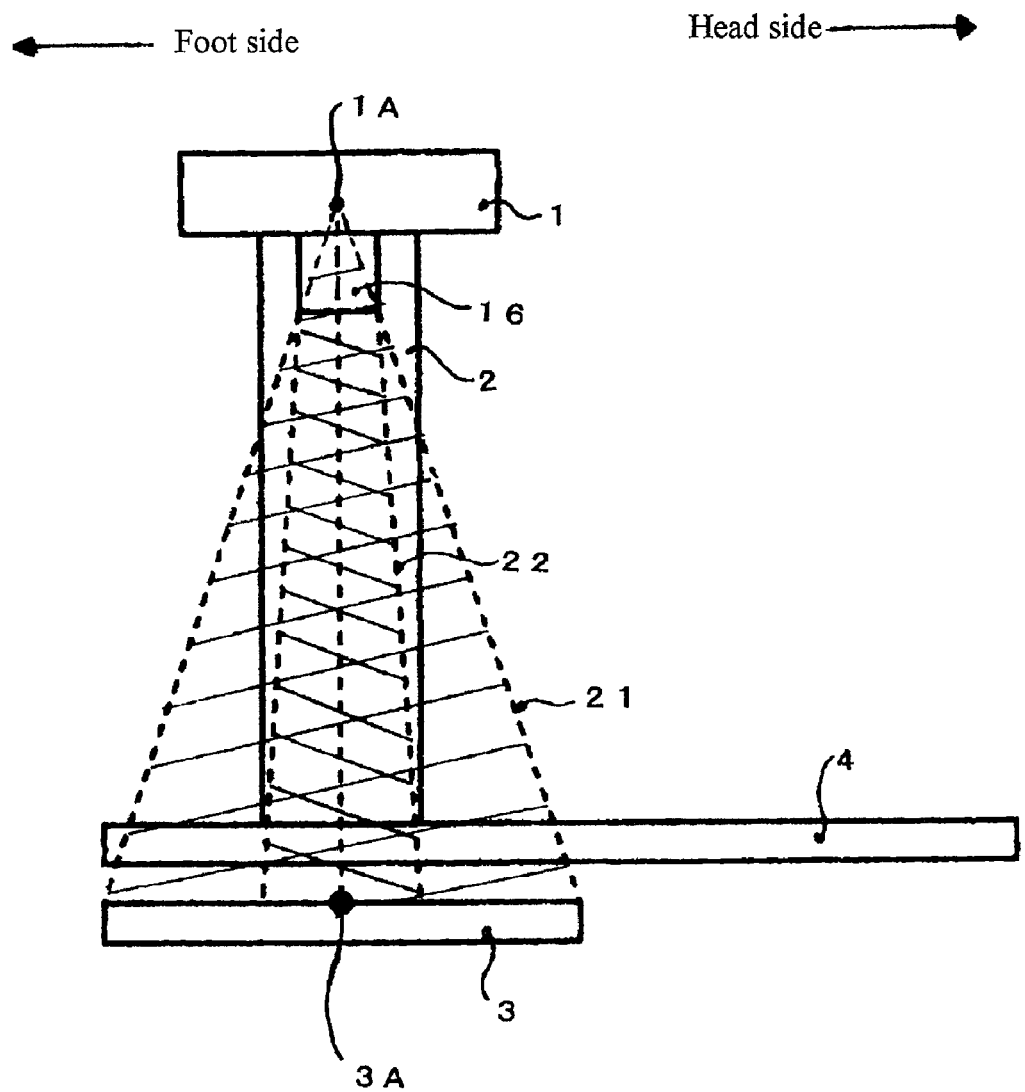
FIG. 12 is a view for expressing motions of a fluoroscopy in the prior art.

In addition, in FIG. 1, when the foot side end of the X-ray image detector 3 is located on the foot side end of the table top 4, and the X-ray tube device 1 is located on the position marked by the real lines, if the operator operates the operation panel 20 as shown in FIG. 3 to move the X-ray image detector 3 towards a head side parallel to the table top 4, the X-ray tube device 1 moves towards the head side while maintaining a state that the foot side end of the irradiation field is consistent with the foot side end of the X-ray image detector 3. In addition, the reference numerals in FIGS. 1 and 5 the same as that in FIG. 12 indicate the same parts as that in FIG. 12, so that the descriptions thereof are omitted.

In the first embodiment, considering the moving motions of the X-ray tube device 1 and the X-ray image detector 3, it is switched between interlocking the X-ray tube device 1 and the X-ray image detector 3 to enable the focal point of the X-ray tube device 1 to come to directly above the central position of the X-ray image detector 3 and interlocking the X-ray tube device 1 and the X-ray image detector 3 to enable the foot side end of the irradiation field to be consistent with the foot side end of the X-ray image detector 3, according to whether the "digestive organ inspection" or the "urinary organ inspection" is selected on the inspection menu screen. However, a change-over switch may be disposed on the operation panel 20 etc., so that the switching motion is performed by using the change-over switch.

In the first embodiment, if the "urinary organ inspection" is selected, the main body control section 12 shown in FIG. 3 controls the X-ray diaphragm 16 through the collimator driving control section 10, so as to adjust the size of the irradiation field while maintaining the two ends of the irradiation field to be respectively consistent with the two ends of the X-ray image detector 3. Alternatively, any one or two of the X-ray tube device 1 and the X-ray image detector 3 are moved in such a way that the foot side end of the irradiation field is consistent with the foot side end of the X-ray image detector 3 while the size of the irradiation field remains unchanged.

Second Embodiment

Figure 6:
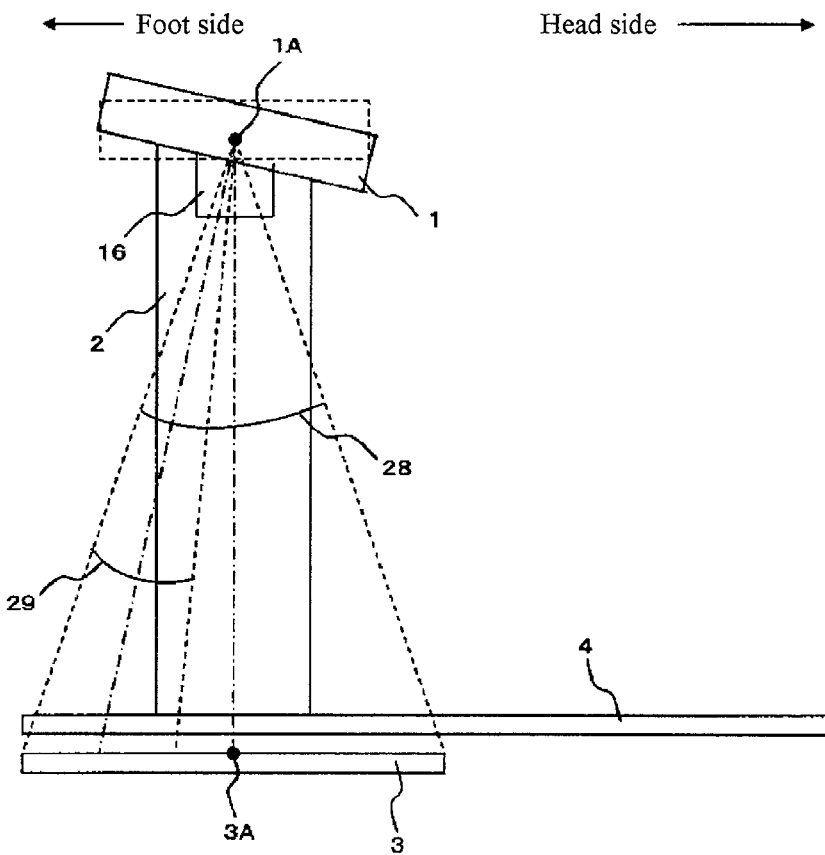
FIG. 6 is a view for expressing motions of a fluoroscopy according to a second embodiment of the present invention.
Figure 7:
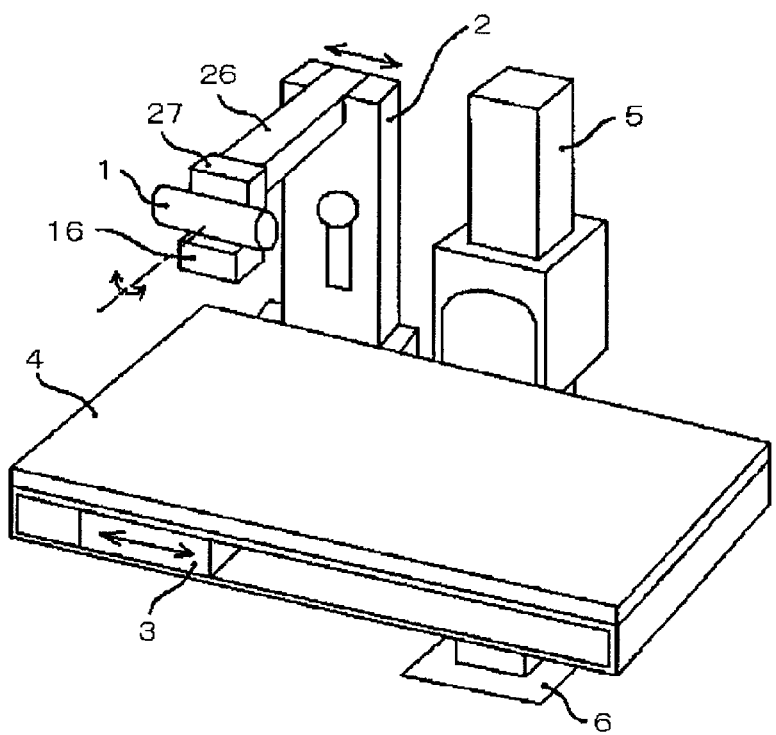
FIG. 7 is a structural view of the fluoroscopy according to the second embodiment of the present invention.
Figure 8:
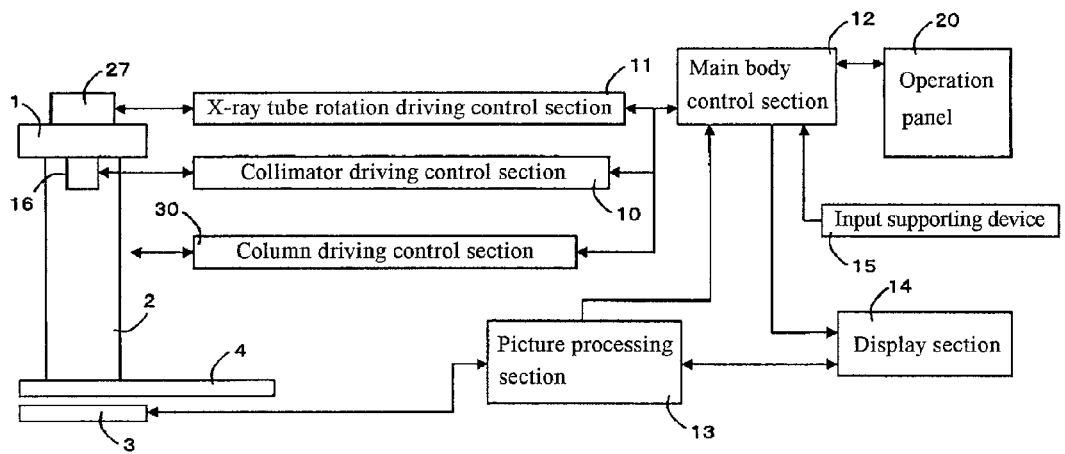
FIG. 8 is a block diagram for expressing motions of the fluoroscopy according to the second embodiment of the present invention.

Referring to FIG. 4 and FIGS. 6 to 9, the second embodiment of the present invention is described. FIG. 7 is a view of an external appearance of a fluoroscopy according to the second embodiment of the present invention. FIG. 8 is a block diagram for demonstrating a control section for controlling the characteristic motions of the second embodiment of the present invention and an operation section. In addition, FIG. 4 is a view of a displaying example of a display section 14, and FIG. 6 is a view for demonstrating a position relation between an X-ray tube device 1 and an X-ray image detector 3 being interlocked with each other.

As shown in FIG. 7, the fluoroscopy according to the second embodiment of the present invention includes, for example, a table top 4, an arm 26, an X-ray tube device 1, an X-ray diaphragm 16, an X-ray image detector 3, etc. The table top 4 is held by using a main column 5 vertically standing on a floor through a base 6, so as to carry a subject (not shown). The arm 26 is mounted on a column 2 movably held in a length direction of the table top 4 by using the main column 5. The X-ray tube device 1 is rotatably held by using an X-ray tube rotation driving section 27 arranged on a front end of the arm 26. The X-ray diaphragm 16 is mounted on an X-ray irradiating section of the X-ray tube device 1 and opens or closes a rectangular irradiation field. The X-ray image detector 3 is arranged on a back side of the table top 4 opposite to the X-ray tube device 1, and is movably held in the length direction of the table top 4 by using the table top 4, and includes, for example, a flat-panel-type X-ray detector or a cassette having a built-in film. The X-ray image detector 3 is supported in such a way that a focal point (not shown) of the X-ray tube device 1 is arranged directly above a central position of the X-ray image detector 3.

Furthermore, the operator (not shown in FIG. 8) selects the "digestive organ inspection" from the inspection menu, for example, shown in FIG. 4 and displayed in the display section 14 as shown in FIG. 8 by operating an input supporting device 15 formed by, for example, a mouse to move a cursor 14A. Then, the operator operates the operation panel 20, such that the X-ray image detector 3 and the X-ray tube device 1 are moved parallel to the table top 4. At this time, a main body control section 12 formed by, for example, a microcomputer, controls an X-ray tube rotation driving control section 11, a collimator driving control section 10, and a column driving control section 30, so as to perform the control motion by maintaining an X-ray center of the X-ray tube device 1 to be located on the central position of the X-ray image detector 3.

Therefore, as shown in FIG. 6, when one end of the X-ray image detector 3 comes to one end of the table top 4, a focal point 1A is located on a position of the X-ray tube device 1 directly above the central position of the X-ray image detector 3 (a detector center 3A), that is, the position and an angle of the X-ray tube device 1 marked by dashed lines become a moving limiting position on one side of the X-ray tube device 1. In the digestive organ contrasting inspection, the position and the angle do not cause a region of interest for the photography to be located in vicinity of the end of the table top 4, so as to fully assure a moving area required by the X-ray tube device 1.

In FIG. 8, the X-ray tube rotation driving control section 11, the collimator driving control section 10, and the column driving control section 30 receive position information signals from their respective moving amount detectors (not shown), and give feedbacks for the signals, such that the main body control section 12 performs a moving amount control. The signal of the X-ray image detector 3 is displayed in the display section 14 after being processed by a picture processing section 13, and is transmitted to the main body control section 12 for being saved. In addition, the reference numerals in FIG. 8 the same as that in FIG. 7 indicate the same parts as that in FIG. 7, so that the descriptions thereof are omitted.

In another aspect, when urinary organ contrasting inspection is performed by using the fluoroscopy according to the second embodiment of the present invention, after the operator selects the "urinary organ inspection" from the display screen as shown in FIG. 4 in the same manner, the main body control section 12 shown in FIG. 8 controls a rotation angle of the X-ray tube device 1 and the X-ray diaphragm 16 through the X-ray tube rotation driving control section 11 and the collimator driving control section 10, so as to adjust a size of the irradiation field while maintaining two ends of the irradiation field to be respectively consistent with two ends of the X-ray image detector 3 when the rotation angle is 0. When the "urinary organ inspection" is selected, the main body control section 12 controls the X-ray tube device 1, the X-ray image detector 3, and the X-ray diaphragm 16 to be always interlocked to enable a foot side end of the irradiation field to be consistent with a foot side end of the X-ray image detector 3.

Under this state, in order to perform the photography on the subject (not shown in FIG. 8) carried in vicinity of a foot side of the table top 4, the operator operates the operation panel 20, such that the X-ray image detector 3 is moved towards the foot side in parallel to the table top 4, and the X-ray image detector 3 is moved till it reaches the position that the foot side end of the X-ray image detector 3 comes to the foot side end of the table top 4 as shown in FIG. 6. At this time, the X-ray image detector 3 is moved till it reaches the position of the X-ray tube device 1 marked by the dashed lines.

Then, the operator operates the operation panel 20 to reduce the size of the irradiation field. After an irradiation field 28 is altered to, for example, an irradiation field 29, the main body control section 12 controls the rotation angle of the X-ray tube device 1 and the X-ray diaphragm 16 through the X-ray tube rotation driving control section 11 and the collimator driving control section 10, such that the X-ray tube device 1 is moved while maintaining the foot side end of the irradiation field to be consistent with the foot side end of the X-ray image detector 3. Therefore, the X-ray tube device 1 is rotated from the position marked by the dashed lines in FIG. 6 when the rotation angle is 0 towards the position marked by the real lines with the focal point 1A as a center. That is to say, the angle of the X-ray center is moved from being vertical to approach a vicinity of the foot side. At this time, the X-ray diaphragm 16 is not rotated. In addition, the numeral 2 represents the column.

Figure 9:
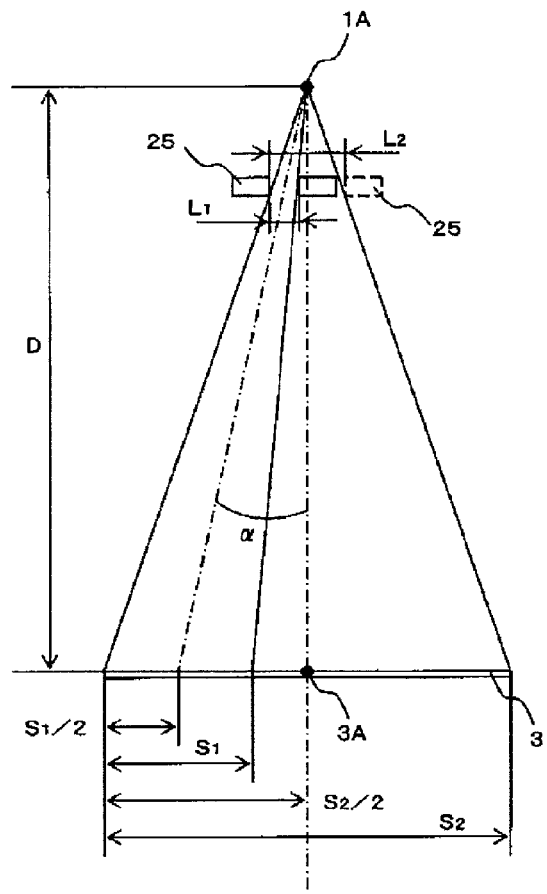
FIG. 9 is a view of a relation between an opening change of an X-ray diaphragm and a rotation angle of an X-ray tube device according to the second embodiment of the present invention.
Figure 10:
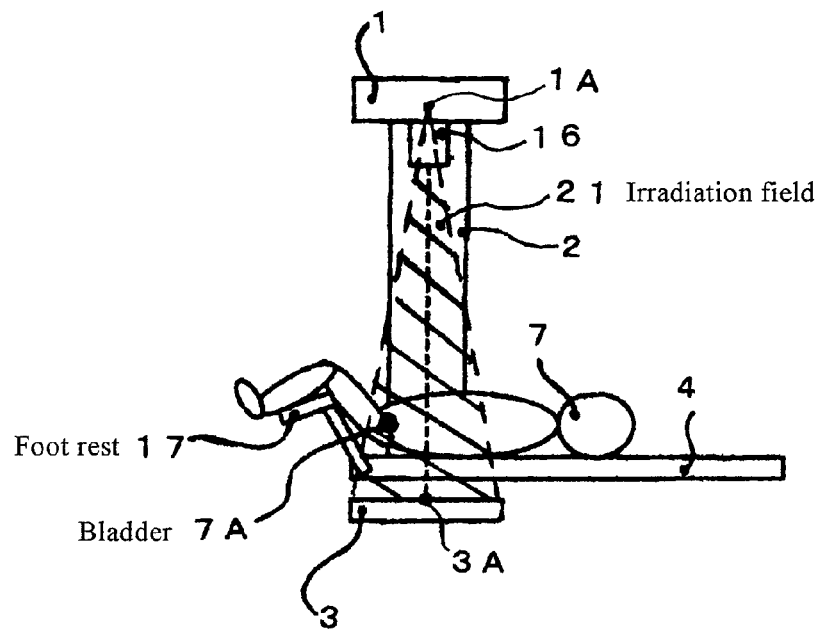
FIG. 10 is a view of performing photography on urinary organs.
Figure 11:
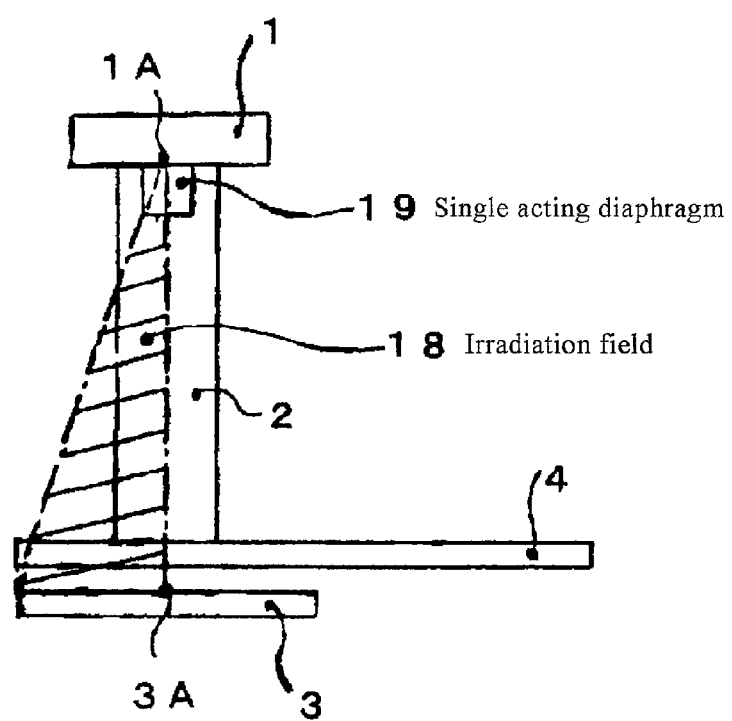
FIG. 11 is a view of a single acting diaphragm.

FIG. 9 shows a geometrical system diagram for calculating a rotation angle α of the X-ray tube device 1 and an aperture width L1 between two leaves 25 when the irradiation field is altered from S2 (the irradiation field 28) to S1 (the irradiation field 29). The two leaves 25 are built in the X-ray diaphragm 16 (shown in FIG. 7), and are formed by X-ray shields for determining the irradiation field. The reference numerals in FIG. 9 the same as that in FIG. 6 indicate the same parts as that in FIG. 6, so that the descriptions thereof are omitted. It is assumed that a distance between a focal plane and an X-ray detecting plane is made to be D, a length of the X-ray image detector 3 is made to be S2, and the aperture width between the leaves 25 is made to be L2 when the irradiation field is S2, and the numerical values are inherent numerical values of the devices and saved in the main body control section 12 shown in FIG. 8. The main body control section 12 reads the numerical values, and calculates the rotation angle α of the X-ray tube device 1 and the aperture width L1 between the leaves 25 according to the following Equation (2) and Equation (3). The main body control section 12 controls the X-ray tube rotation driving control section 11 to enable the rotation angle of the X-ray tube device 1 to be only moved for α, and controls the collimator driving control section 10 to enable the aperture width between the leaves 25 to be L1.

$$\alpha = \operatorname{Tan}^{-1}(S2/2 - S1/2)/D \qquad \text{Equation (2)}$$

$$L1 = L2 \times S1/S2 \qquad \text{Equation (3)}$$

The corresponding result is as shown in FIG. 6, and after the foot side end of the X-ray image detector 3 comes to the foot side end of the table top 4, the X-ray tube device 1 is rotated and the irradiation field is narrowed down by the X-ray diaphragm 16, and the control motion is performed to enable the foot side end of the irradiation field to be consistent with the foot side end of the X-ray image detector 3. Therefore, even in the urinary organ contrasting inspection when the region of interest for the photography is located in vicinity of the foot side end of the table top 4, as compared with the fluoroscopy in the prior art, the subject (not shown in FIG. 6) is prevented from being over-irradiated. Furthermore, since the photography is performed by using the X-ray beams located close to the X-ray center, a picture having less serious picture blurring and less serious picture distortion is obtained.

In the second embodiment, regarding the control on the X-ray tube device 1 and the X-ray diaphragm 16, whether it is switched to either controlling the X-ray tube device 1 and the X-ray diaphragm 16 to enable the rotation angle of the X-ray tube device 1 to be maintained to 0 and to enable the center of the irradiation field to be consistent with the center of the X-ray image detector 3 or rendering the X-ray tube device 1 and the X-ray diaphragm 16 to be interlocked to enable the foot side end of the irradiation field matches the foot side end of the X-ray image detector 3 when the irradiation field is altered, it depends on whether the "digestive organ inspection" or the "urinary organ inspection" is selected on the inspection menu screen. However, a change-over switch may be disposed on the operation panel 20 etc., so that the switching operation is performed by using the change-over switch. In addition, the X-ray diaphragm 16 is not a structure capable of being rotated, but if the X-ray diaphragm 16 is a structure capable of being rotated together with the X-ray tube device 1, the present invention may also be implemented. As described above, the present invention is not limited to the demonstrative embodiments, but includes variation embodiments.

INDUSTRIAL APPLICABILITY

The present invention relates to a fluoroscopy.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A fluoroscopy, comprising:
    a table top, for carrying a subject;
    an X-ray tube, movably held in a body axis direction of the subject parallel to the table top;
    an X-ray image detector, arranged opposite to the X-ray tube by sandwiching the table top there-between, and being movable in the body axis direction of the subject parallel to the table top; and
    an X-ray diaphragm, mounted on the X-ray tube and forming a rectangular X-ray irradiation field;
    wherein the fluoroscopy further comprises:
    a control means, for performing a control in one of a first control manner and a second control manner, wherein in the first control manner, the X-ray tube and the X-ray image detector are moved parallel to the table top in such a way that a focal point of the X-ray tube is located directly above a center of the X-ray image detector, and in the second control manner, when the X-ray irradiation field is altered on ends of the X-ray tube and the X-ray image detector being moved to a foot side of the subject parallel to the table top, the X-ray tube is moved in such a way that a foot side end of the X-ray irradiation field and a foot side end of the X-ray image detector are overlapped; and
    a control manner assigning means, for assigning the control means to perform the control in the first control manner or in the second control manner.

2. The fluoroscopy according to claim 1, wherein a camera part assigning means for assigning a camera part in the first control manner or in the second control manner according to the camera part also serves as the control manner assigning means.

3. The fluoroscopy according to claim 1, wherein the control manner assigning means is a change-over switch.

4. A fluoroscopy, comprising:
    a table top, for carrying a subject;
    an X-ray tube, movably and rotatably held in a body axis direction of the subject parallel to the table top;
    an X-ray image detector, arranged opposite to the X-ray tube by sandwiching the table top there-between, and being movable in the body axis direction of the subject parallel to the table top; and
    an X-ray diaphragm, mounted on the X-ray tube and forming a rectangular X-ray irradiation field;
    wherein the fluoroscopy further comprises:
    a control means, for performing a control in one of a first control manner and a second control manner, wherein in the first control manner, the X-ray tube and the X-ray image detector are moved parallel to the table top in such a way that a focal point of the X-ray tube is located directly above a center of the X-ray image detector, and in the second control manner, when the X-ray irradiation field is altered on ends of the X-ray tube and the X-ray image detector being moved to a foot side of the subject parallel to the table top, the X-ray tube is rotated in such a way that a foot side end of the X-ray irradiation field and a foot side end of the X-ray image detector are overlapped; and
    a control manner assigning means, for assigning the control means to perform the control in the first control manner or the second control manner.

5. The fluoroscopy according to claim 4, wherein a camera part assigning means for assigning a camera part in the first control manner or in the second control manner according to the camera part also serves as the control manner assigning means.

6. The fluoroscopy according to claim 4, wherein the control manner assigning means is a change-over switch.

* * * * *